United States Patent [19]

Anbar

[11] 4,022,876

[45] May 10, 1977

[54] MASS SPECTROMETRIC IMMUNOASSAY

[75] Inventor: Michael Anbar, Palo Alto, Calif.

[73] Assignee: Stanford Research Institute, Menlo Park, Calif.

[22] Filed: June 21, 1973

[21] Appl. No.: 372,197

[52] U.S. Cl. .................................. 424/1; 23/230 B; 250/282; 250/303; 424/12; 424/1.5

[51] Int. Cl.[2] .................. G01N 33/16; G21H 5/02; B01D 59/44

[58] Field of Search ................ 424/1, 1.5; 250/282, 250/303; 23/230 B

[56] References Cited

UNITED STATES PATENTS

| | | | |
|---|---|---|---|
| 3,663,684 | 5/1972 | Freedman et al. | 424/1 |
| 3,666,854 | 5/1972 | Eisentraut | 424/1 |
| 3,697,638 | 10/1972 | Hansen | 424/1 |
| 3,776,698 | 12/1973 | Eisentraut | 424/1 X |

OTHER PUBLICATIONS

Radioimmunoassay Methods, ed Kirkham et al., 1970, pp. 405–412.

*Primary Examiner*—Benjamin R. Padgett
*Assistant Examiner*—Christine M. Nucker
*Attorney, Agent, or Firm*—Lindenberg, Freilich, et al

[57] ABSTRACT

A method and means of making an immunological assay is provided whereby stable isotopes of certain elements, or long-lived radioisotopes of these elements are used to tag antigens or antibodies. A known amount of the tagged antibodies or antigens are then mixed with the unknown number of antigens or antibodies forming an antigen-antibody complex, (bound) and free tagged antigens, or antibodies, (unbound). The bound antigens or antibodies are separated from the unbound, and their quantity is determined by negative ion mass spectrometry. An aliquot of the unbound or bound antigens or antibodies is taken and dried in a metal crucible, for example, which is then inserted into a negative ion mass spectrometer where the sample is vaporized, ionized and the number of tagging atoms is then counted. From the information provided by the count, an immunoassay can be established.

6 Claims, 3 Drawing Figures

MASS SPECTROMETRIC IMMUNOASSAY

BACKGROUND OF THE INVENTION

This invention relates to a new method and means for detecting and assaying of various pathogens, toxins, drugs, or hormones, or their antibodies and more particularly to improvements therein.

A large number of clinical tests are based on radioimmunoassay, which is an extension of fluorescent immunoassay as well as of isotope dilution analysis. These tests include primarily the assay of a large number of hormones, primarily polypeptides, such as parathyroid or human growth hormone, as well as steroid hormones. The same methods can be extended, however, to the detection and assay of various pathogens or toxins and in fact of any drug or chemical that can be conjugated with a protein. The antibodies of these species can be assayed in a similar manner. The method is highly specific and highly sensitive and replaces bioassay methods as well as clinical analysis when very minute amounts of material have to be determined.

The methodology of radioimmunoassay has been reviewed many times and there have been recently published two volumes on the topic, one of which is *Radioimmunoassay Methods*, by Kirkham and Hunter, and published by Churchill Livingston, Edinburgh (1971). The other is *Principles of Competitive Protein Binding Assays*, by Odell and Daughaday, published by J. B. Lippincott & Co., Philadelphia (1971). In principle the radioimmunoassay comprises mixing a known amount of radioisotope labeled antigen (or antibody) with a solution carrying antibodies (or antigens), the quantity of which is desired to be determined. The labeled antigens (or antibodies) combined with the unlabeled antibodies (or antigens) in a known ratio. The labeled antigens (or antibodies) which combined with unlabeled antibodies (or antigens) are called bound, and the labeled antigens (or antibodies) which are not combined, are called unbound. The unknown concentration of the antigen (or antibody) in the sample solution is then derived from the ratio of the bound to unbound labeled tracer antigens (or antibodies). In all cases, it is necessary to separate the bound complex from the unbound labeled antigen or antibody and to determine the amount of the radioisotope in one of these forms as a function of concentration. Of the numerous methods of separating the unbound material from the bound complexes, the adsorption onto solid particles and the double antibody technique are the most popular. The radioactivity may be assayed in the supernatant or in the solid phase. Radioactivity is determined in the usual manner, using a Geiger counter, for example.

The labeling of polypeptide or conjugated protein antigens, or of antibodies, with a radioactive tracer has, however, serious limitations and drawbacks. The ultra-high sensitivity required by this methodology (determination of subnanogram quantities of proteins) makes it imperative to use short lived isotopes at as high a specific activity as possible. It is evident, therefore, that the labeled antibodies or antigens have a rather short half-life, not only because of the limited physical half-life of the labeling radioisotope but also because of the artoradiolytic damage to the labeled protein molecules, which may readily lead to their inactivation. The practical half-life of such labeled antibodies is, therefore, only a few days, and poses a severe limitation on the whole methodology. In fact, radio-immunoassay is limited today to research laboratories capable of synthesizing the labeled antibodies or antigens, purifying the labeled protein without loss of immunological activity, and assaying it at frequent intervals to assure its antigenic activity.

OBJECTS AND SUMMARY OF THE INVENTION

It is an object of this invention to provide a method and means of determining the number of labeling atoms in a given sample of bound or unbound antigen, or antibody, without the use of radioactivity for purposes of detection.

Yet another object of this invention is to provide a method and means of making a radio-immunoassay wherein the labeled antibodies or antigens have a long life and are not subjected to autoradiolytic damage.

Still another object of the present invention is the provision of a method and means for making a radioimmunoassay with a greater accruacy than was possible to perform heretofore.

Another object of this invention is to provide a method for identifying a particular antibody (or antigen) from among a number of possibilities by performing a single assay with a number of different antigens (or antibodies) each labeled with a different identifying label.

The foregoing and other features of the invention are achieved by preparing a label antigen, or antibody, which then can be titrated in well known manner, with a solution containing an unknown amount of the antigen, or antibody, to produce a solution whose concentration or antigens (or antibodies) is to be determined. The labeling atoms may be stable or radioactive, but the radioactivity is not used for detection of the labeling atoms. They may include atoms of elements not normally associated with proteins, such a bromine, fluorine, selenium or tellurium or isotopes of elements present in proteins such as chlorine, carbon, or hydrogen. The bound complex is separated from the unbound in well known manner. An aliquot of the separated material is then placed in the input section of a negative ion mass spectrometer. There, the sample is atomized and then specific negative ions are formed. The label on the protein or protein complex may also be converted into an inorganic form, such as copper halide, prior to introduction into the ionization source of the mass spectrometer.

Negative ion formation may be accomplished by several well known methods such as by the use of a hot plasma produced in a discharge type ion source. Another way to produce specific negative ions is by the interaction of the vaporized, molecules with a hot metal surface (contact ionization). An example of such an ionization source incoroprates a heated thoriated tungsten filament as electron donor. Another example of such an ionization source uses a porous metal structure through which the volatized sample passes prior to being ionized on the outer surface. These negative ions are extracted from the source, mass analyzed, and counted.

The preferred stable isotopes are those whose negative ion assay is not affected by high background caused by negative ions derived from the protein being analyzed, or from sporadic impurities therein. Carrier-free long lived radioisotopes may be preferred because of their extremely low natural background. Illustrative of the preferred isotopes are $^{129}$I, $^{79}$Se (to be measured as SeH$^-$), $^{36}$Cl, $^{14}$C, and $^3$H, for example. Long lived radioisotopes such as $^{129}$I ($t_{1/2} > 10^7$ years), Cl$^{36}$ ($t_{1/2} > 10^5$ years), or Se$^{79}$ ($t_{1/2} > 7 \times 10^4$ years), or even C$^{14}$ ($t_{1/2} > 5 \times 10^3$ years) may be considered as stable isotopes for practical purposes. $^{127}$I, $^{74}$Se, $^{120}$Te, $^{133}$Te (to be measured as TeH$^-$), $^{81}$Br, $^{37}$Cl, and $^{19}$F are reasonaby good labels though their background may be somewhat higher than that of the former group of isotopes.

DESCRIPTION OF THE PREFERRED EMBODIMENTS

Figure 1:
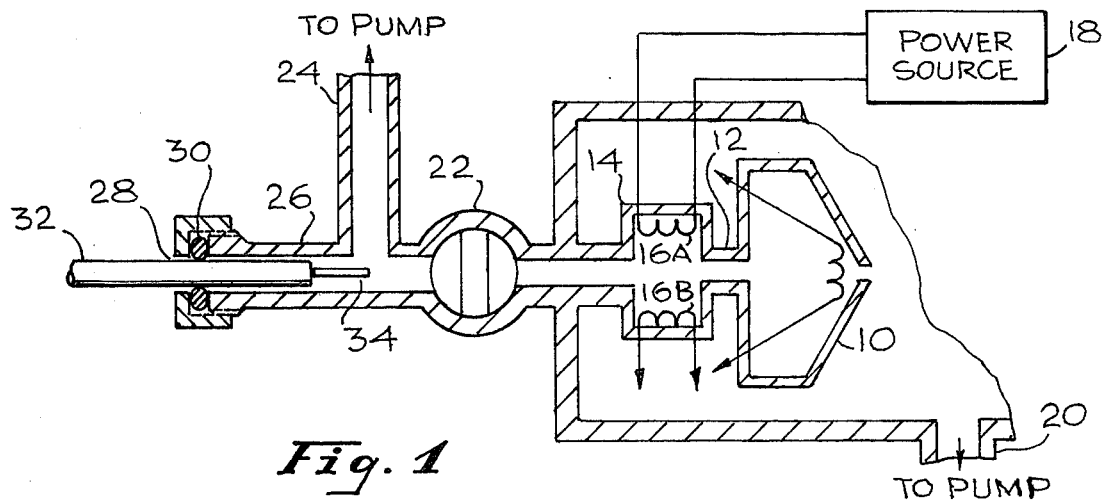
FIG. 1 is a schematic drawing, illustrating the input section of a mass spectrometer, in accordance with this invention, before the insertion of a sample to be analyzed.

In accordance with this invention, tagging of an antigen or antibody with a nonradioactive isotope such as $^{127}$I, for example, is carried out by exposing the antigen or antibody to $^{127}$I in the presence of an oxidizer. A sample of an antigen or antibody to be assayed is prepared in the same manner, as for radioimmunoassay, except that labeling for immunoassay is performed using as tracers, stabel isotopic atoms or long lived radioisotopes that are absent in the normal antibody or antigen proteins. Exampes of these isotopes, which are preferrred, are the ones which are not subject ot background noise caused by other negative ions present in the specimen being analyzed. Preferred stable isotopes, as previously indicatd, are exemplified by $^{127}$I and $^{129}$I if necessary, $^{81}$Br, $^{36}$Cl, $^{74}$Se, $^{79}$Se, $^{120}$Te, $^{133}$Te, $^{14}$C, as well as tritium.

The methods used at present in radioimmunoassay are adaptable to the preparation of samples for use in mass spectrometry which is the technique to be used in accordance with this invention. By way of illustration, a known amount of a tagged antigen is added to a solution containing the unknown amount of antibodies. The tagged antigens and antibodies combine in a known ratio so that if one can count the number of tagged antigens, from this count, one can determine the number of antibodies that are present. Usually, an excess of tagged antigens is added to the solution to isnure that there are enough to combine with all of the unknown antibodies present. If the solution containsan unknown amount of antigens, then antibodies are tagged and added to the unknown solution as described.

After the preparation of the sample, whose unknown concentrations of antigen (or antibody) is desired to be determined, it is necessary to separate the bound from the unbound antigens (or antibodies). The sample may have a supernatant liquid which is separated from the remainder. The remainder contains the unbound labeled antigens (or antibodies). An aliquot is taken from the remainder and dried in a metal crucible. The contents of the curcible are inserted into the input section of a negative ion mass spectrometer where they are vaporized, and then entered into the ionization source of the mass spectrometer. Alternatively, an antigen-antibody complex may be adsorbed onto a large metal surface, such as a sintered metal filter, and after the supernatant is washed off, this may be dried, vaporized and the vapor directed into the ionization source of the mass spectrometer. Another technique is to adsorb the antigen-antibody complex on dispersed particulates (such as charcoal, talc, or pretreated cellulose). This dispersion is then filtered by a coarse sintered metal filter, washed, dried, vaporized and directed into the ionization chamber. Still anothe technique is to convert a halogen or chalcogen carrying protein into an inorganic form such as copper iodide or copper selenide and introduce the latter into the mass spectrometer negative ion source.

Referring now to FIG. 1, there may be seen in schematic form, the input section of a negative ion mass spectrometer in accordance with this invention. Reference numberal 10 indicates the plasma generating section of the negative ion mass spectrometer. Coupled thereto via a passageway 12 is a pyrolysis oven 14. This pyrolysis oven has electric heater wires 16A, 16B therein, which are connected to a power source 18.

In order to maintain a vacuum at this input section to the mass spectrometer, passageways are provided, indicated by reference numeral 20 which couple this input section to the vacuum pump. A "see through" valve 22, enables insertion of a specimen from outside of the mass spectrometer into the pyrolysis oven. In FIG. 1, this see through valve is shown in its closed position. It is a well known type of valve which is adjustble from the outside to enable the introduction of a sample into the pyrolysis oven.

A "vacuum roughing" passageway 24 is provided for enabling the drawing of an initial vacuum in the section of tubing 26 which connects the input port 28 to the see through valve. The input port has a sealing ring 30, made of a suitable plastic material which enables a rod 32 to move therethrough while holding sufficiently tightly to the rod to preserve a "rough vacuum". The rod 32 carries at its end a crucible 34, in which the sample to be analyzed by the negative ion mass spectrometer is placed.

Figure 2:
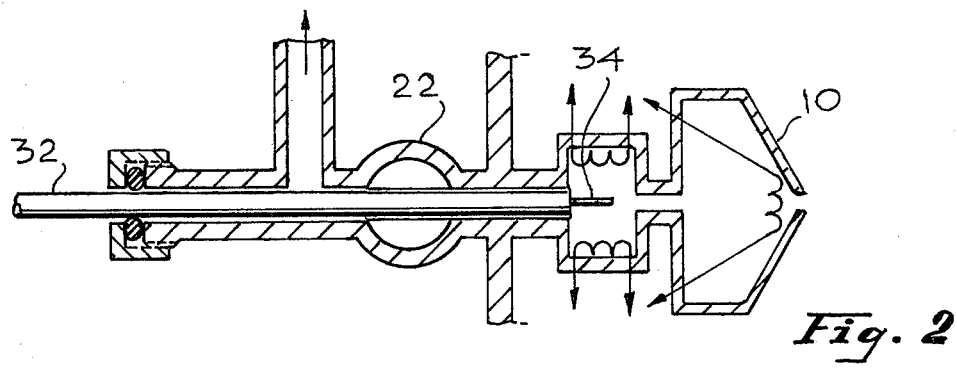
FIG. 2 is a schematic drawing of the input section of a mass spectrometer in accordance with this invention, illustrating the appearance when a sample to be analyzed has been inserted therein.

FIG. 2 shows the appearance of the see through valve 22 after the crucible 34, which is carried by the rod 32, has been introduced into the pyrolysis oven. The valve is lined with a plastic sleeve which adheres to the surface of the rod sufficiently so that the vacuum pumps can still maintain a vacuum.

Figure 3:
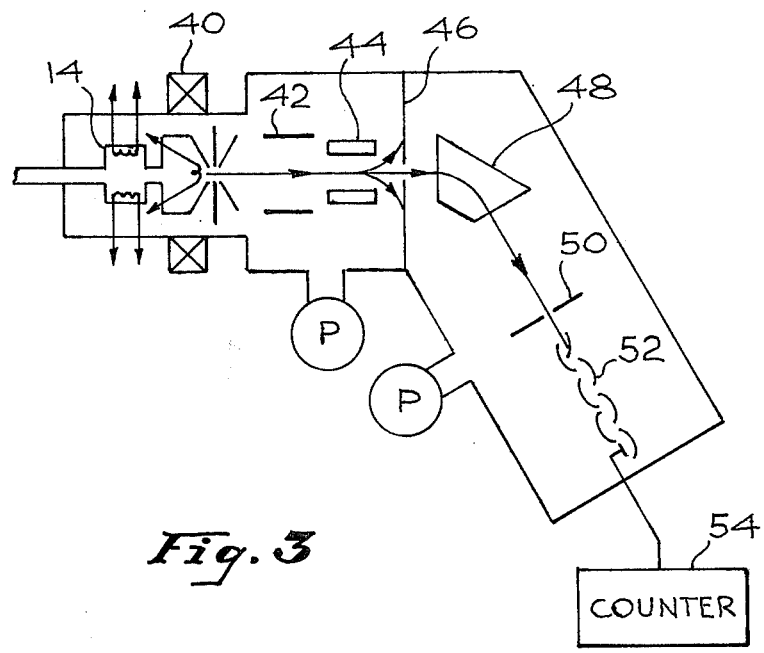
FIG. 3 is a schematic diagram illustrating a negative ion mass spectrometer which is used in an immunoassay in accordance with this invention.

FIG. 3 is a schematic view illustrating the remainder of the negative ion mass spectrometer. This is conventional. It includes a source magnet 40 which is used to separate the electrons which occur at the negative ion source 41 from the negative ions. The negative ions pass through an aperture into a region between focusing electrodes 42. The negative ions thereafter pass through a Wien velocity filter 44. The Wien filter "velocity selects" the negative ions. It produces a combined electric and magnetic field which are normal to each other and to the ion beam direction. An ion with a correct velocity will experience equal but opposite electric and magnetic forces as it passes through the filter and hence, will not be deflected as are the other ions with incorrect velocities. A diaphragm 46 has a hole therethrough. The undeflected ions pass through the hole whereas the other deflected ions are intercepted by the diaphragm. The mass resolution of this filter M/ΔM can vary from 0 to about 40, and its purpose is to remove most of the unwanted components of the ion beam before they enter the magnetic deflection field. This arrangement eliminates a major source of noise caused by unwanted ions that are scattered into the detector by collision with ambient, background gas particles.

A magnetic mass deflector 48 sets up a deflection field and thus acts to further deflect and separate the wanted from the unwanted ions. The wanted ions are deflected in passing through the magnetic mass separator so that they can pass through an apertur in another membrane 50. Thereafter, the halogen ions enter an electron multiplier detector region 52, the output of which actuates a counter 54. The count of the counter indicates the amount of separated antigens (or antibodies).

The sample bearing crucible is inserted into the entry portion of the mass spectrometer and can be position programmed so that the sample in the crucible is volatized at a rate that is slow enough to prevent overloading of the ion source. The volatized sample gases undergo further fragmentation as well as ionization in the hot plasma of the ion source. Halide atoms tend to break from their parent molecule and form stable negative ions because of their large electron affinity ($> 3$ eV). Selenium and tellurium tend to form $SeH^-$ and $TeH^-$ respectively (which also have high electron affinity); carbon forms $CN^-$ ions (which has a comparable electron affinity). In the case of plasma discharge type ion source, a constant flow of a buffer gas such as Ar or $N_2$ may be maintained in the ionization region to sustain the plasma discharge in the ion source. These gases are especially suitable because they do not form stable negative ions and are not corrosive. The negative ions produced in the source plasma are extracted and formed into a beam of about 5 keV energy. No buffer gas is required for the case of a hot metal surface ion source. The latter source is incapable, however, to produce a representative amount of $CN^-$ or $H^-$ ions. The efficiency of halide negative ions beam production for both source types is estimated to be at least 1 in $10^3$ of the halogens on sample molecules but may be as high as 1 in 100.

An an alternative to forming negative ions in a hot plasma, if desired, the vaporized molecules of the sample may be made to interact with a hot metal surface (contact ionization) in well known manner to provide ions.

The use of antigens or antibodies labeled with nonradioactive halogens or the other "uncommon" atoms for immunoassay have four very important advantages.

1. The labeled antigens or antibodies have substantially "infinite" stability. The lifetime of the labeled protein is thus determined only by denaturation processes, which is normally many years. This would eliminate the necessity of synthesizing the labeled materials in individual laboratories, with all the complications resulting from impure radiotracer preparations. Large quantities of well purified and well calibrated labeled antigens or antibodies could thus be produced in central research or commercial laboratories and distributed to all users. The use of nonradioactive labels or labels of very low radioactivity allows large scale synthesis even with lower yields of the highly purified immunological active materials.

The loss of immunological activity on labeling is a major problem. The use of labeling reactions that do not involve oxidative halogenation may produce higher yields of immunologically unmodified materials. Incorporation of halogenated pheynylalanine, tyrosine, or thyronine into the desired protein can be performed; acetylation with $CT_3Co$, $^{14}CH_3CO$, or $CH_2^{36}ClCO$ may be another. Enzymatic synthetic procedures may also be used.

2. A large number of possible labels are available. The proposed methodology is not restricted by the availability of radioactive isotopes, $^{131}I$ and $^{125}I$ are currently in use. The use of at least 12 different atomic labels of at least 8 elements is possible.

The option of different labeling atoms would also allow the simultaneous assay of a number of antigens (or antibodies). Some sensitivity may be lost in this procedure because different label atoms will have to be monitored by the mass spectrometer intermittently, using a programmed mass selector. However, a number of hormones could be determined from a single sample in a shorter time. This may be critical in experiments on small animals or if hormone assay is to be carried out on tissues rather than on plasma or urine.

3. The higher sensitivity attainable by the method allows the extension of immunoassay beyond its present limitations. Antibody labeling in particular may benefit from its sensitivity. The immunoradiometric assay methodology, which is impractical today because of lack of sensitivity could thus become a routine method.

4. The herein described method can be readily automated. An automatic sample changer can be introduced into the vacuum system of the ionization source. Since the counting time per sample will be shorter (for the same precision) than in radioimmunoassay, it is conceivable that 20 samples, required for a reliable assay, can be measured within 30 minutes. Thus, over a dozen assays might be carried out in a normal working day. This is faster than possible today by radioassay.

There has accordingly been described and shown herein a novel and useful method and means for performing an immunoassay on antigens and antibodies.

What is claimed is:

1. The method of making an immunological assay of a sample contining an unknown amount of an antigen or antibody comprising:

preparing a solution containing a known amount of one of said antigens or antibodies, when the sample contains the other, tagged with a stable isotope or a long lived radioisotope, mixing said sample with said solution to produce a mixture of tagged bound and unbound antigens or antibodies, separating said bound from said unbound, and applying said bound or said unbound to a negative ion mass spectrometer for counting the number of ions of tagging material whereby the amount of antigens or antibodies in said sample are determined.

2. The method of making an immunological assay of a sample containing either an unknown amount of antigens or of a sample containing an unknown amount of antibodies, comprising:

preparing a solution containing a known amount of antibodies or antigens tagged with a stable isotope or a long lived radioisotope, mixing said solution of a known amount of tagged antibodies with said unknown antigen sample or mixing said sample of said known amount of tagged antigens with said unknown antibody sample, to produce either a solution having bound and unbound tagged antibodies, or a solution having bound and unbound antigens, separating said bound from said unbound in each of said solutions, and applying an aliquot of said separated bound or unbound to a negative ion mass spectrometer for isolating and counting the number of tagging material ions to indicate the amount of antigens or antibodies present in the sample.

3. The method as recited in claim 2 wherein said tagging material is one of a group consisting of $^{129}$I, $^{36}$Cl, $^{79}$Se, $^{133}$Te, and $^{14}$C.

4. The method as recited in claim 2 wherein the step of counting the tagged antigens or antibodies includes:

vaporizing an aliquot of sid bound or unbound tagged antibodies or antigens, ionizing said vaporized aliquot to form negative ions of the material with which said antigens or antibodies were tagged, separated said negative ions from the remainder, and counting the number of said negative ions.

5. The method of making an immunological assay of a solution containing an unknown amount of antigens or a solution contining an unknown amount of antibodies, comprising:

preparing a solution of a known amount of antibodies or antigens tagged with a stable isotope or a long lived radioisotope, mixing said solution of a known amount of tagged antibodies with said unknown antigen solution or said known amount of tagged antigens with said unknown antibody solution to produce either a solution having bound and unbound tagged antibodies, or a solution having bound and unbound antigens, in each of said solution separating said unbound from said bound, vaporizing an aliquot of one of said bound or unbound for each of said solution, ionizing said vaporizing aliquot for each of said solutions, separating the ions of said stable isotope from all others in said ionized vaporized aliquot, and counting said number of ions of said tagging material from which count the unknown amount of antigens or antibodies may be derived.

6. The method as recited in claim 2 wherein said stable isotope of one of a group consisting of $^{129}$I, $^{36}$Cl, $^{79}$Se, $^{133}$Te, $^{14}$C, and $^{3}$H.

* * * * *